United States Patent [19]

Beckhaus et al.

[11] Patent Number: 4,720,326
[45] Date of Patent: Jan. 19, 1988

[54] PROCESS FOR WORKING-UP AQUEOUS AMINE SOLUTIONS

[75] Inventors: Heiko Beckhaus, Brunsbüttel; Harro Witt, Kuden; Dieter Becher, Dormagen; Hermann Dallmeyer, Leverkusen; Uwe J. Zarnack, Brunsbüttel, all of Fed. Rep. of Germany

[73] Assignee: Bayer Aktiengesellschaft, Leverkusen, Fed. Rep. of Germany

[21] Appl. No.: 14,759

[22] Filed: Feb. 13, 1987

[30] Foreign Application Priority Data

Mar. 8, 1986 [DE] Fed. Rep. of Germany ....... 3607665

[51] Int. Cl.$^4$ .............................................. B01D 3/00
[52] U.S. Cl. ...................................... 203/14; 203/25; 203/39; 203/78; 203/98; 203/99; 203/DIG. 8; 203/DIG. 19; 564/437
[58] Field of Search ........................ 203/14, 25, 12, 21, 203/39, 98, 99, 71, DIG. 8, DIG. 19, 73, 78; 202/202, 204; 564/437

[56] References Cited

U.S. PATENT DOCUMENTS

| | | | |
|---|---|---|---|
| 3,032,586 | 5/1962 | Dierichs et al. | 564/422 |
| 3,194,839 | 7/1965 | Robinson et al. | 502/185 |
| 3,223,731 | 12/1965 | Craig et al. | 564/437 |
| 3,356,728 | 12/1967 | Cimerol et al. | 564/422 |
| 3,356,729 | 4/1964 | Denton et al. | 564/423 |
| 3,420,752 | 1/1969 | Kirss et al. | 564/437 |
| 3,421,983 | 1/1969 | Buchsbaum | 203/14 |
| 3,431,085 | 3/1969 | Cimerol et al. | 422/200 |
| 3,433,788 | 3/1969 | Somekh et al. | 203/14 |
| 3,441,586 | 4/1969 | Luberoff et al. | 564/437 |
| 3,546,296 | 12/1970 | Gobron et al. | 564/422 |
| 3,761,521 | 9/1973 | Alheritiere et al. | 564/422 |
| 3,882,048 | 5/1975 | Thelen et al. | 502/333 |
| 3,895,065 | 7/1975 | Alheritiere et al. | 564/489 |
| 4,032,411 | 6/1977 | Tornquist et al. | 203/14 |

FOREIGN PATENT DOCUMENTS

| | | | |
|---|---|---|---|
| 0273220 | 4/1965 | Australia | 564/437 |
| 2106644 | 8/1972 | Fed. Rep. of Germany . | |
| 2135154 | 2/1973 | Fed. Rep. of Germany . | |
| 1005056 | 1/1986 | Japan | 564/437 |
| 0982483 | 2/1965 | United Kingdom | 564/437 |
| 1017646 | 1/1966 | United Kingdom . | |
| 1490313 | 11/1977 | United Kingdom . | |
| 0243625 | 9/1969 | U.S.S.R. | 564/437 |

*Primary Examiner*—S. Leon Bashore
*Assistant Examiner*—V. Manoharan
*Attorney, Agent, or Firm*—Gene Harsh; Joseph C. Gil; Lyndanne M. Whalen

[57] ABSTRACT

An amine is separated from an aqueous solution of amine and volatile organic compounds by distillation in a column. The vapors generated during distillation are condensed. The condensed vapors are then passed into a separating device in which the volatile organic compounds are removed. The liquid remaining in the separating device is then fed to the head of the distillation column. Water is removed from the column in a sidestream and diamine is the residue. This process is particularly effective in recovering aromatic diamines from solutions which accumulate during hydrogenation of dinitro aromatic compounds.

9 Claims, No Drawings

PROCESS FOR WORKING-UP AQUEOUS AMINE SOLUTIONS

BACKGROUND OF THE INVENTION

The present invention relates to a new distillation process for working-up aqueous amine solutions.

It is well known (See, for example, DE-OS Nos. 1,542,544, 1,947,851, 2,106,644, 2,135,154, 2,214,056, 2,456,308; BE-PS Nos. 631,946, 661,047, 661,946; FR-P No. 1,359,438 and GB-P No. 768,111) that it is possible to produce aromatic diamines by catalytic hydrogenation of the appropriate aromatic dinitro compounds. The hydrogenation can take place with the aid of solvents such as alcohols which boil at a low temperature (e.g., methanol, ethanol, or isopropanol) and also without such solvents. The hydrogenation may be carried out with catalysts which are dispersed in the reaction mixture during the reaction and then separated off by sedimentation or filtration and, as necessary, re-used.

Up to now, the working-up of such reaction mixtures has taken place in such a way that the mixture of aromatic diamines and reaction water present after any adjuvant solvent used has been separated off is continuously freed of water under normal pressure in a distillation column. The diamine accumulates as a distillation residue and water which adheres to the diamine and any organic impurities which might still be present are separated from the residue in additional steps. Mixtures of water with organic by-products which are volatile in steam, such as those that accumulate in the hydrogenation of the dinitro aromatic substances arise as distillates. Examples of such by-products are aromatic or cycloaliphatic monoamines and/or cycloaliphatic alcohols. For example, in the case of the production of diaminotoluene, toluidines, perhydrotoluidines and/or methyl cyclohexanols form as by-products.

These by-products which are volatile in steam have the effect of causing the water distilled off overhead to be loaded heavily with these compounds. Removal of those by-products from the water is possible only at great expense, for example, by using a biological clarifier.

It is an object of the present invention to make available a new process for the working-up of aqueous amine solutions in which the waste water contains less organic impurities.

This and other objects which will be apparent to those skilled in the art are accomplished by the process of the present invention which makes it possible for the energy which has been spent on evaporating the water to be largely reclaimed by using the heat of condensation of the vapors.

DETAILED DESCRIPTION OF THE INVENTION

The subject matter of the invention is a process for working-up aqueous amine solutions such as those which accumulate in the catalytic hydrogenation of aromatic dinitro compounds. More particularly, it relates to the working-up of aqueous amine solutions which contain aromatic diamine compounds and organic compounds which are products of secondary reactions and are volatile in steam by distillation to separate the water, together with the organic by-products which are volatile in steam, in a distillation column. In this process the vapors of the distillation column are condensed and the fluid phase which accumulates is taken over a separating device. Organic by-products which are volatile in steam are removed from the vapor condensate as an organic phase in the separating device. The aqueous phase leaving the separation device is then taken back onto the head of the distillation column. The water which has been freed of substantially all organic impurities which are volatile in steam is taken away from the distillation column via a sidestream. The diamines which have largely been freed of water and impurities which are volatile in steam are then obtained as a residue.

The starting materials for the process of the present invention are aqueous amine solutions such as those which accumulate in the hydrogenation of dinitro aromatic substances. In this process, aqueous amine solutions which accumulate in the hydrogenation of industrial dinitrotoluenes and which have been freed, beforehand, by distillation, of any adjuvant solvent used in the hydrogenation process (e.g., simple alcohols) are preferably used. These solutions are generally approximately 50–70 wt. % solutions, preferably 55–65 wt. % solutions of diaminotoluenes in water. These solutions generally contain up to 5%, preferably 500–3000 ppm (weight) of impurities which are volatile in steam. These diamines include pure 2,4 diaminotoluene or its industrial mixtures with up to 40 wt. %, based on the total weight, of 2,6 diaminotoluene, and possibly up to 5 wt. %, based on the total mixture, of other isomeric diaminotoluenes whereby the percentages total 100 in each case.

The process of the present invention is carried out in a distillation column, such as a bubble plate column or a packed column. A column having 12 to 40, and preferably 20 to 40 theoretical plates is preferred. The column is operated at a residue temperature of 120° to 210° C., preferably 140° to 180° C., and under a pressure (at the head of a column) of at least one, preferably 1.5 to 6 bar absolute. These parameters obviously depend upon the nature of the mixture to be worked-up and upon the vapor temperature which is desired. The heat of condensation of the vapors can easily be regulated in operations carried out under excess pressure in such a way that it can be used, for example, for the evaporation of solvents, for the warming of product streams or for the generation of process vapor.

The solutions which are to be worked-up by distillation are generally fed into the column at a point above the distillation bottom which is heated (for example, by means of a circulating evaporator), i.e. at least on the second, and preferably at a point between the third and eighth theoretical trays. The vapors are completely condensed during the process of the present invention and after an organic phase has been separated off, they are taken back into the head of the column. The distillate is removed by means of a removal plate via a side stream which is fitted onto at least 4, preferably 5 to 15 theoretical trays underneath the head of the column, and at least 8, preferably 12 to 25 theoretical trays above the bottom of the column. In this process the volume ratio of reflux (below the removal point) to removal is at least 0.3, preferably 0.4 to 0.6.

If the distillation column is operated continuously under these conditions, the organic by-products which are volatile in steam enrich themselves to a surprising degree in the column head and, as soon as their concentration rises above the limit of solubility in water, they can be removed from the vapor condensate with a separating device.

This separating device which is installed between the evaporator condenser and the column head in the reflux pipe can, for example, be a phase separator. It is also possible, however, to remove partly or totally the organic impurities present in the vapor condensate by sedimentation, centrifuging, adsorption by adsorbents or extraction from the vapor condensates before it is taken back into the column head. The water which is drawn off in the sidestream is only very slightly contaminated by organic compounds.

The water which accumulates as a condensate contains up to 5 wt. %, preferably from 0,2 to 5 wt. % and most preferably from 2 to 5 wt. % of organic by-products. In the simple distillation separation of the water from aqueous amine mixtures (such as those which accumulate in the hydrogenation of industrial dinitrotoluenes), the water which is obtained by the process of the present invention from analogous basic mixtures in the form of the sidestream has a level of impurities of this kind of between 10 and 500 ppm (weight).

In the process of the present invention, the aromatic diamines which are largely freed of water are continuously discharged as a residue. The organic substances which are continuously separated off at the head of the column can be further processed as chemical raw materials or burned for power. The water which is removed via the sidestream is so clean that it can be used at many points in chemical processes instead of demineralized water.

The invention is further illustrated but is not intended to be limited by the following example in which all parts and percentages are by weight unless otherwise specified.

EXAMPLE 2 l/h of a reaction mixture which was free of solvents from the dinitrotoluene(DNT)hydrogenation process were fed into a bubble plate column at the fifth plate (DN 50 mm with 30 plates, corresponding to 21 theoretical plates). The mixture was an approximately 60 wt. % solution of a diamine mixture consisting essentially of 77.2 wt. % 2,4 diaminotoluene, 19.3 wt. % 2,6 diaminotoluene and 3.5 wt. % of other diaminotoluene isomers. The solution had a content of organic by-products volatile in steam of 0.3 wt. %. The column was separated under a pressure of 3 bar absolute and at a bottom temperature of approximately 200° C. On the 20th plate (14th theoretical plate) a removal plate with a sidestream removal device was fitted. A sidestream of 750 ml/h of distilled water at a temperature of 133° C., with a content of organic by-products of 200 ppm (weight) was continuously removed. The volume ratio of reflux to withdrawal of (R/E) 0.4 was maintained at this point of the distillation column.

The vapors of the column were condensed and taken back via a phase separator into the head of the column (30th plate). The quantity of the aqueous phase taken back was 1050 ml/h and the quantity of organic phase which had been continuously removed from the phase separator at the same time was 8 ml/h. This organic phase had a water content of 4 wt. %.

The diamine which was obtained continuously as a residue in a quantity of 1240 ml/h still had a residual water content of 3.5%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A distillation process for separating amine from an aqueous amine solution containing an aromatic diamine and an organic by-product which is volatile in steam comprising
    (a) feeding the aqueous amine solution to a distillation column,
    (b) distilling the aqueous amine solution,
    (c) condensing the vapors that were generated during distillation (b),
    (d) removing the condensed vapors obtained in step (c),
    (e) passing the condensed vapors removed in (d) into a separating device in which an organic and an aqueous phase are formed,
    (f) removing the organic by-product volatile in steam as the organic phase,
    (g) returning the aqueous phase remaining after separation in (f) to the head of the distillation column as reflux, and
    (h) removing the water from the distillation column in a sidestream thereby leaving aromatic diamine freed of water and volatile by-products as the residue.

2. The process of claim 1 in which the distillation column has from 12 to 40 theoretical plates.

3. The process of claim 2 in which the sidestream for removing water is at least four theoretical plates below the head of the distillation column and at least eight theoretical plates above the bottom of the distillation column.

4. The process of claim 1 in which the reflux to sidestream removal ratio is at least 0.3.

5. The process of claim 1 in which the amine in the aqueous solution is a diaminotoluene.

6. The process of claim 1 in which the aqueous amine solution is obtained from a process for hydrogenation of dinitrotoluenes in the presence of adjuvant solvent.

7. The process of claim 6 in which the adjuvant solvent is distilled off before the aqueous amine solution is fed to the distillation column in step (a).

8. The process of claim 1 in which the distillation column is maintained at 1.5 to 6 bars absolute pressure.

9. The process of claim 1 in which the energy obtained by condensing the vapors in (c) is used as a heat source for the distillation in step (b).

* * * * *